US005486160A

United States Patent [19]
Rossi et al.

[11] Patent Number: 5,486,160
[45] Date of Patent: Jan. 23, 1996

[54] DEVICE AND METHOD FOR THE COMBINED ELECTROPHARMACOLOGICAL TREATMENT OF THE BLADDER AND THE PROSTATIC URETHRA

[75] Inventors: Cino Rossi, Rome; Silvio Eruzzi, Mantova, both of Italy; Robert L. Stephen, Salt Lake City, Utah; Franco Lugnani, Trieste, Italy

[73] Assignee: Physion S.r.l., Italy

[21] Appl. No.: 237,672

[22] Filed: May 4, 1994

[51] Int. Cl.⁶ .................................................. A61N 1/05
[52] U.S. Cl. ........................... 604/21; 607/40; 607/138
[58] Field of Search .............................. 607/3, 40, 66, 607/116, 138, 148, 99; 604/20, 21, 96

[56] References Cited

U.S. PATENT DOCUMENTS 5,236,413  8/1993  Feiring ............................ 604/20
5,246,437  9/1993  Abela ............................. 604/20
5,286,254  2/1994  Shapland et al. .................. 604/21
5,301,688  4/1994  Stephen et al. ................... 604/20
5,328,451  7/1994  Davis et al. ..................... 604/21

Primary Examiner—Lee S. Cohen
Assistant Examiner—Brian M. Green
Attorney, Agent, or Firm—Jacobson & Johnson

[57] ABSTRACT

Device for the combined electropharmacological treatment of the bladder and the prostatic urethra including a bougie comprising a flexible tubular body, openings for connection to the outside, an opening in its tip and elastic sealing elements arranged perimetrically around it, the bougie being internally provided with a stem-like electrode having two independent conductors, one shorter than the other, and suitable to perform a combined electropharmacological treatment of the bladder and of the prostatic urethra.

16 Claims, 3 Drawing Sheets

DEVICE AND METHOD FOR THE COMBINED ELECTROPHARMACOLOGICAL TREATMENT OF THE BLADDER AND THE PROSTATIC URETHRA

BACKGROUND OF THE INVENTION

The present invention relates to a device for the combined electropharmacological treatment of the bladder and the urethra.

The electropharmacological treatment better known as Electromotive Drug Administration (EMDA) relates to the transfer of solutes (drugs) into the body tissues by means of an electromotive force. In particular, the term "electromotive drug administration" includes two separate physical processes: iontophoresis and electrophoresis.

Devices suitable to perform a iontophoretic treatment aimed at the bladder or at the urethra are currently adopted, such devices using a bougie inside which there is an electrode that is appropriately connected to a source of electric current. One or more drugs in solution are introduced through said bougie proximate to the region to be treated, and their ions are then activated by producing an appropriate electric field by means of a low-voltage current source and by applying to the body of the patient, proximate to the region to be treated, an external secondary electrode suitable to close the electric circuit.

The same Applicants have solved the problem of concentrating the action of this therapy in a point by providing a device for intracorporeal iontophoresis, the particular aim whereof is to treat deseases affecting the bladder, filing for this device a related Italian patent application no. MI/21107 on Jul. 27, 1990 which discloses a tubular body that is internally crossed, in a position that is substantially concentric with respect to its longitudinal axis, by a stem-like electrode which forms, at its distal end, a sort of helical spring ending with a spheroidal ground electrode; the body of the bougie is appropriately affected by multiple openings which are suitable to allow the instillation of the drug in the organ to be treated and the flow of the current for activating the ions of said drug.

This iontophoretic device has the drawback of using a bougie that is intended to specifically treat the bladder alone and is not suitable to simultaneously treat affections of the prostate, an organ which is often involved, together with the bladder, in affections of the lower urinary tract.

Currently there is no specific device for the electropharmacological therapeutic treatment of affections involving both the bladder and the prostate. For this purpose it is only possible to adapt iontophoretic devices by subjecting the patient to the insertion of two different bougies, each of which is shaped so as to be suitable for treating the target organ. This treatment has the drawback that it causes, due to the sequential insertion of the two bougies, painful physical microtraumas in tissues that are already the seat of inflammatory processes.

Furthermore, it is in any case necessary to replace the internal electrode, the conducting portion whereof is limited to the region to be treated and is in any case unable to generate differentiated intensities of current in the two different organs. This maneuver for replacing the electrode entails both discomfort for the patient and an increase in the duration of the bougienage for the patient.

SUMMARY OF THE INVENTION

Accordingly, one of the most important objects of the present invention is to provide a device suitable to perform a simultaneous "in situ" electropharmacological treatment of the bladder and of the prostatic urethra.

A further object of the invention is to provide a device that allows to simultaneously produce two different electromotive forces suitable to guide the drug(s) in different manners toward the two target organs (bladder and prostate).

An additional object of the present invention is to provide a method for electropharmacological treatment that is aimed at curing affections that simultaneously affect the bladder, the prostatic urethra and the prostate itself, providing an in situ treatment that allows to administer high but differentiated amounts of the proximately principle according to the severity of the affections involving the target organ (bladder-prostate).

Another object of the present invention is to provide a therapeutic treatment method that allows to administer a high concentration of proximate principles directly to the organs that form the lower and medium urinary tract, minimizing the side effects that would occur by administering through other pathways an amount of drug suitable to produce a tissue concentration, in said organs, equal to the concentration obtained by using the device according to the present invention.

With this aim in view, as well as these and other objects which will become apparent hereinafter, there is provided, according to the present invention, a device for the combined electropharmacological treatment of the bladder, urethra and prostate comprising a bougie formed by a flexible tubular body which is provided, at its proximal end, with a connector having at least one inlet, said body having, at its distal end, openings for connection to the outside, an opening in its tip and elastic sealing means arranged perimetrically around it, said bougie being internally provided with an electrode that comprises at least two independent conductors that slide axially, each conductor having an insulated portion and conducting portions that are mutually spaced.

Preferably, the conducting portion of at least a first one of said conductors is located at the distal end of said bougie, and the conducting portion of at least a second one of said conductors is located at the proximal end of the bougie; the conducting portion of said second conductor is furthermore preferably shaped like a spiral and can be coiled around the insulated portion of said first conductor.

Advantageously, the conducting portion of said first conductor has, at its distal end, a multidirectional ground electrode that can be extracted through the opening in the tip of the tubular body; said multidirectional ground electrode preferably comprises a spherical core which is rigidly coupled to the end of said conductor and from which multiple elastically flexible conducting spokes extend radially.

Preferably, the above described electropharmacological treatment device entails the use of said conductors that can be powered independently of one another; more preferably, said conductors are two, and even more preferably one is shorter than the other. Advantageously, the conducting portion of said shorter conductor is spiral-shaped and can be coiled around the insulated portion of the second conductor.

Advantageously, said longer conductor has, at its distal end, a multidirectional ground electrode that can be extracted through the opening in the tip of the tubular body; more preferably, said multidirectional ground electrode includes a spherical core which is rigidly coupled to the end of said conductor and from which a plurality of elastically flexible conducting spokes extends radially.

Said sealing means arranged perimetrically with respect to the bougie of the device are furthermore preferably constituted by a bag that is dilatable during use and that in its active configuration is suitable to obstruct the prostatic urethra upstream of the bladder.

The device according to the present invention allows to provide a method for the simultaneous electropharmacological treatment of the bladder and of the urethra, including the steps of:

placing the bougie along the urethra so that its distal end enters the bladder, inserting the electrode, which is divided into at least two independent conductors of different lengths, so as to allow the end of the longer conductor to pass through the opening of the tip to allow the multidirectional ground electrode to open out radially inside the bladder and, simultaneously, arranging the second conductor along the prostatic urethra, applying a second external counter-electrode in an external body region at the organs to be treated, electrically connecting said electrode to an external circuit that includes an electric current source connected to the external counter-electrode, infusing a solution that comprises at least one drug suitable to treat affections involving the bladder and the prostate and, simultaneously, applying a potential difference between said electrodes, thereby producing an electric field suitable to cause the migration of said at least one drug into the tissues of the bladder and of the prostate.

Advantageously, the current applied to said conductors is supplied at different potential values, in order to allow a differentiated migration of the dissolved ions; in particular, the electrode located at the more severely affected organ is supplied with a higher voltage, allowing to administer a larger amount of drug to the tissues that most need to be treated.

Furthermore, by using the above described device it is possible to supply a large amount of solution of the drug that can dilate the tissue of the bladder and fill the cavity of the bladder so that it can act as a vessel for containing the solution that subsequently flows out through the prostatic urethra, allowing further therapeutic treatment of the urethral tissue.

The application of an electric field to a solution of a drug administered by means of the bougie according to the present invention ensures that the rate of diffusion of the drug through the tissues is accelerated and can be controlled simply by varying the intensity of the electric current and/or the time for which it is applied to the individual conductor. Furthermore, application of an electric current following the instillation of a pharmaceutical solution both in the bladder and in the prostatic urethra ensures that the drug is released both through the urothelium and through the prostatic tissue, producing high concentrations of proximate principle(s) in these tissues.

In particular, the above described therapeutic method can be used to successfully treat a wide range of affections of the lower and medium urinary tract by using, in each instance, the drug or a mixture of different proximate principles that is considered most suitable for curing the disease. By way of example, in the treatment of interstitial cystitis it is possible to use antiinflammatory steroid drugs such as for example hydrocortisone sodium hemisuccinate, prednisolone sodium phosphate, methylprednisolone sodium succinate betamethasone sodium phosphate, in association with local anaesthetics such as lidocaine hydrochloride, procaine hydrochloride, mepivacaine hydrochloride, etc., with antispastic drugs such as trimebutine maleate and with antibiotics such as for example ampicillin, gentamicin, ceftriaxone, etc. The treatment method is particularly suitable for performing local anticancer therapy, and allows to achieve high concentrations of anticancer agents such as for example mitomycin C, mithramycin, doxorubicin etc., considerably reducing the well-known general toxicity problems.

By way of example, 100 ml of Dm Na P in a 0.01–0.05% aqueous solution are instilled in the bladder along the prostatic urethra, applying a current of 6–9 mA at the bladder and 4–5 mA at the prostate, with current application times of 10 and 5 minutes respectively, using an electrode with two conductors according to the present invention, thus providing an effective anti-inflammatory treatment.

By way of further example, it has been found that periodic treatment with 40 mg of mitomycin C infused in an 0.9% saline solution, using the device according to the present invention, has allowed to treat cancer forms localized in the prostate and in the bladder with good tissue response, avoiding high blood concentrations of the anticancer drug. In particular, by applying inside the bougie an electrode which is constituted by two anodic conductors the first one whereof is shorter than the other and is arranged at the prostatic urethra and the second one is long enough to exit from the urethral canal, allowing its distal end—provided with a center from which a plurality of conducting spokes extends—to exit into the cavity of the bladder, an iontophoretic/electrophoretic treatment has been provided that entails the infusion, through the bougie, of a solution of mitomycin C and the application of a differentiated current of 10 and 15 mA respectively at the prostate and at the bladder, with an application time of 10 minutes.

BRIEF DESCRIPTION OF THE DRAWINGS

Further characteristics and advantages of the device for the combined electropharmacological treatment of the bladder and of the urethra according to the present invention will become apparent from the following detailed description of a preferred but not exclusive embodiment thereof, illustrated only by way of non-limitative example in the accompanying drawings, wherein.

DESCRIPTION OF THE PREFERRED EMBODIMENTS

Figure 1:
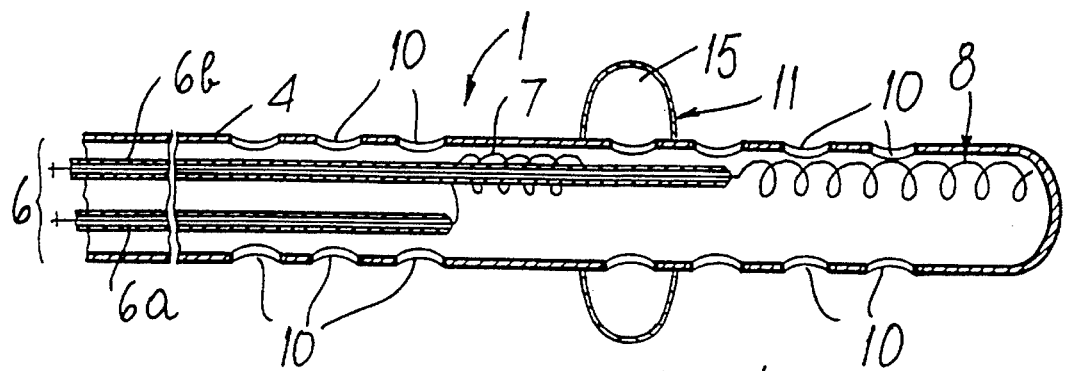
FIG. 1 is a schematic sectional detail view, in enlarged scale, of a bougie according to the present invention.
Figure 2:
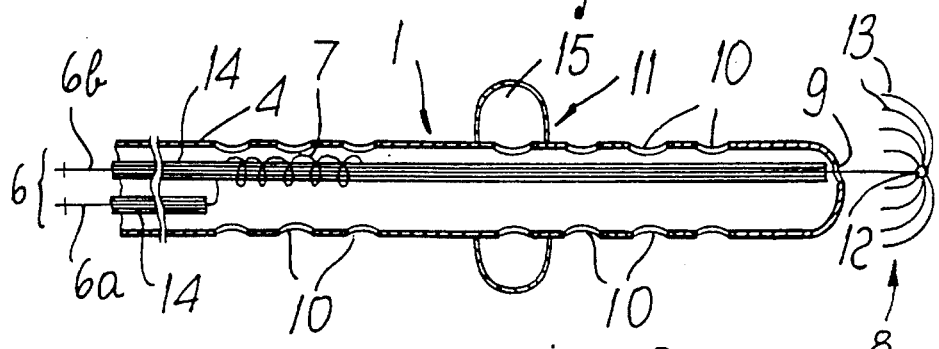
FIG. 2 is again a sectional view of a detail of the distal portion of said bougie.
Figure 3:
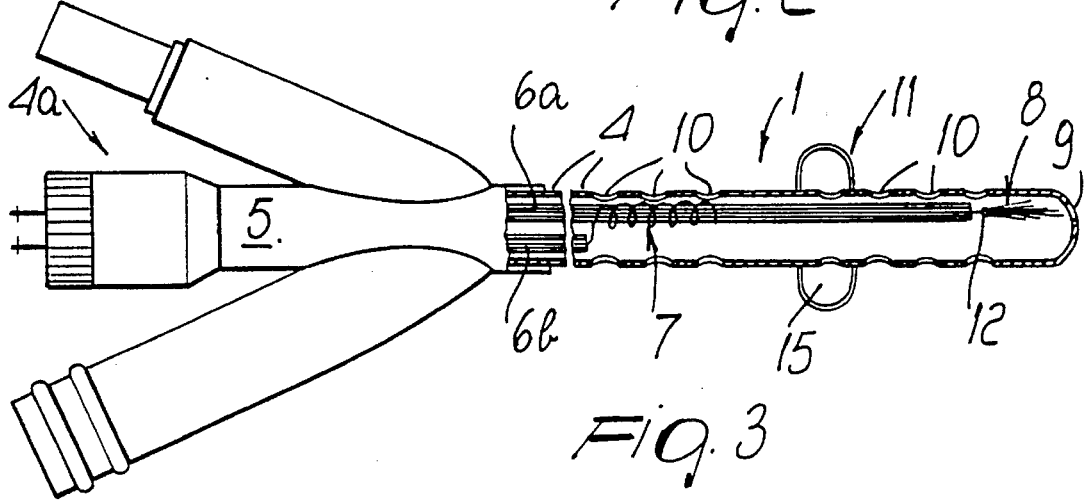
FIG. 3 includes the distal and proximal ends of the bougie according to the invention, again in a sectional view.
Figure 4:
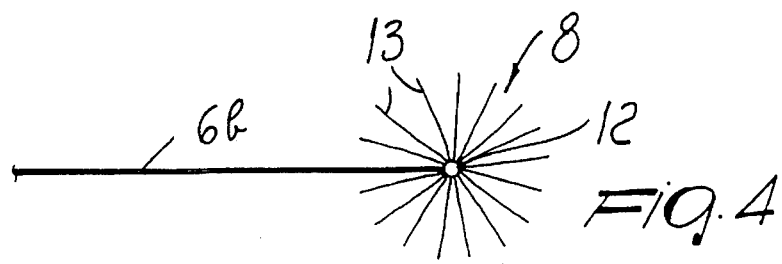
FIG. 4 is a detail view of the distal end of the conductor, which has the radial multidirectional ground electrode (8) at its end.
Figure 5:
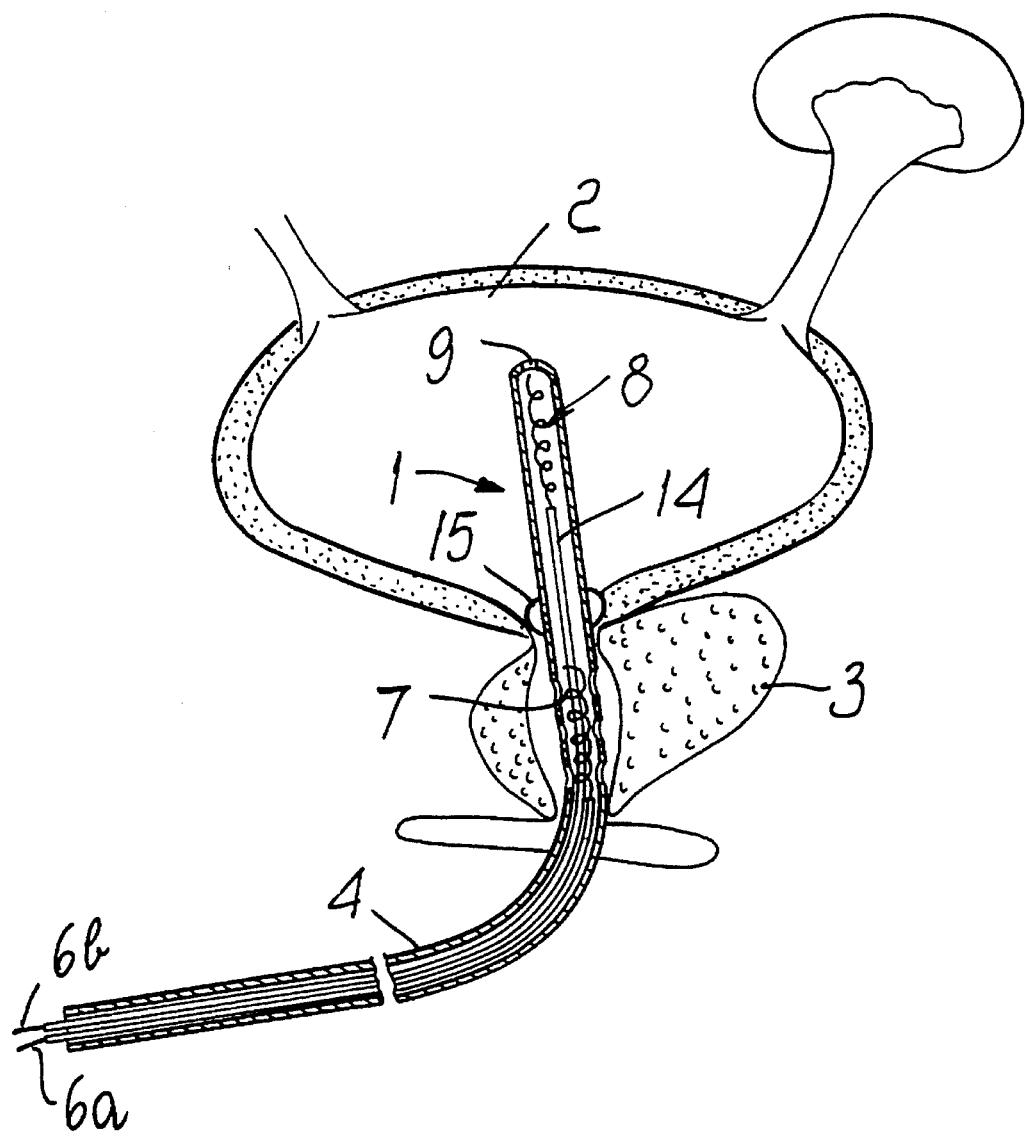
FIGS. 5 and 6 are views of the bougie according to the present invention in two possible embodiments, in position for use.
Figure 6:
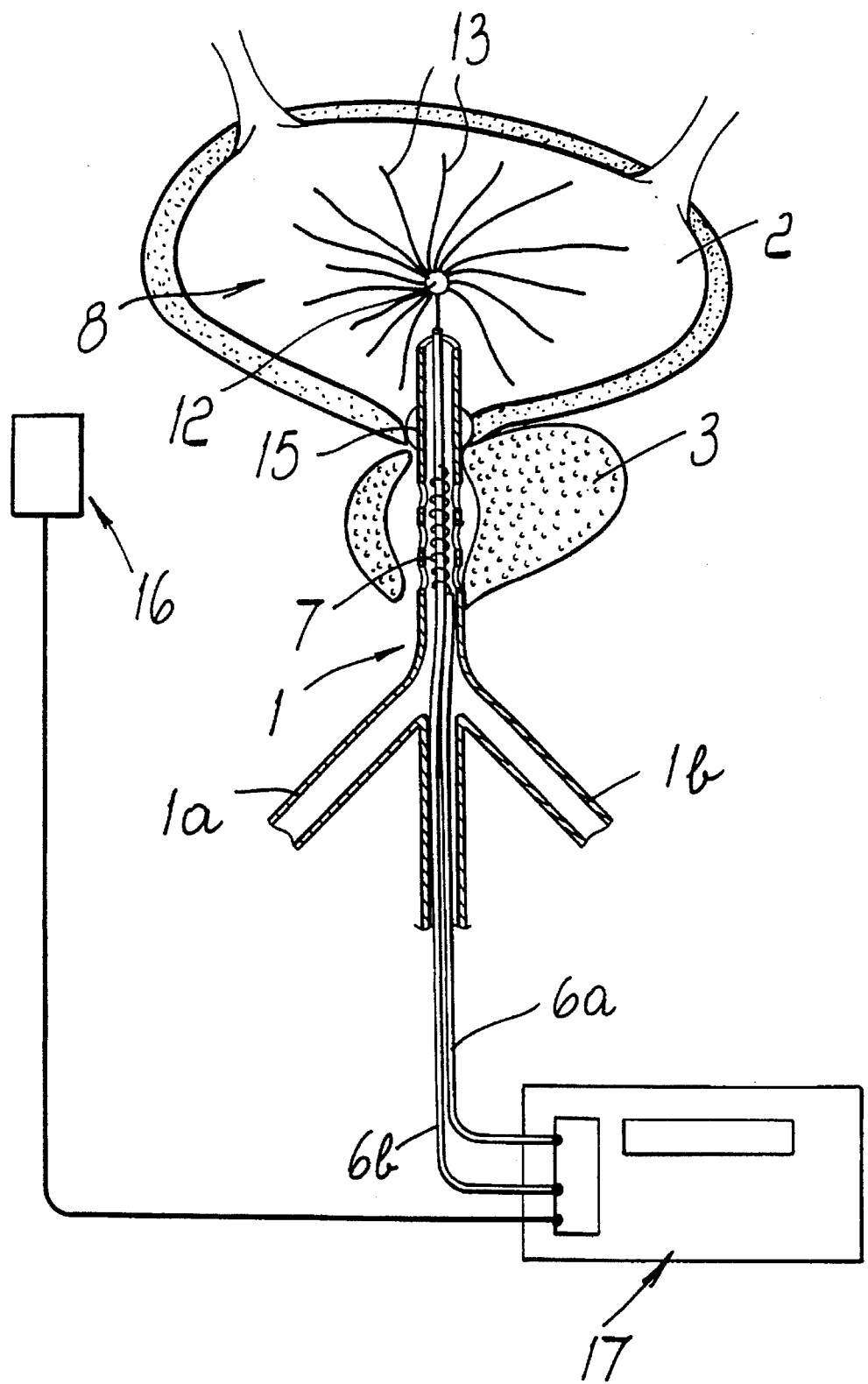

With particular reference to the above figures, the reference numeral 1 generally designates a bougie for the combined electropharmacological treatment of the bladder 2 and of the urethra 3, which is constituted by a body 4 having a tubular shape with a flexible structure and having, at its proximal end 4a, a connector 5 with multiple inlets.

A stem-like electrode 6 passes inside the bougie 1 and is in turn divided into at least two linear, mutually independent and substantially parallel conductors 6a, 6b; the first conductor 6a is shorter than the second one 6b, and said first conductor 6a has, at its distal end, which is located at the urethra 3 when the bougie 1 is fully inserted, a terminal 7 that can be coiled around the second conductor 6b, which is in turn axially slideably mounted within the tubular body 4 and has, at its distal end, a multidirectional ground electrode 8 that can be extracted from the tubular body 4 through an opening 9 formed in the tip, said distal end being located inside the bladder when the bougie is fully inserted. In the distal portion of the tubular body 4 there are openings 10 that are connected to the outside; perimetrically mounted elastic sealing means 11 are furthermore applied in a transverse section of the tubular body 4 that is comprised between the distal ends of said first and second conductors.

Said multidirectional ground electrode 8 is constituted by a spherical center 12 that is rigidly connected to the distal end of the second conductor 6b and from which multiple thin, flexible and conducting spokes 13 extend, preferably in a radial direction; the set of said spokes preferably forms a spherical/hemispherical volume.

In order to ensure the mutual independence of the conductors 6a and 6b, each of them is protected with its own insulating sheath 14 that covers it along its entire length except for its distal end.

The elastic sealing means 11 are preferably constituted by at least one bag 15 that can be dilated as required and is suitable to close the passage section of the urethra 3.

The power supply 17 has a connection for three current lines: two form the two sheathed conductors 6a and 6b that enter the bougie, and the third line 6c is routed so as to supply power to the secondary electrode 16, which is suitable to be arranged in an external body region proximate to the lower abdomen and/or to the lumbar region of the back.

The use of the embodiment according to the invention as described above provides for the insertion of the bougie 1 in the urethra 3 of a patient in a conventional manner until its distal part reaches the inside of the bladder 2.

In this position, the distal end of the first conductor 6a is substantially located at the urethra 3, whereas the distal end of the second conductor 6b, which is longer, is located substantially at the center of the bladder 2; both conductors 6a and 6b are sheathed with an insulator 14 to avoid mutual contact and to allow them to be crossed by currents having different intensities and optionally with coherent or phase-shifted repetitive cycles.

The second conductor 6b is slideably mounted inside the tubular body 4, so that the ground electrode 8 can be pushed, through the opening 9 provided for this purpose, outside said body 4, thus placing itself at the center of the bladder.

This external protrusion causes the spontaneous spread of the spokes 13 from the center 12; said spokes arrange themselves radially so as to form a sort of diffusion globe or half-globe.

Finally, the bag 11 that closes the urethral duct is inflated.

The drug or medical solution is instilled through one of the openings of the connector 5 and reaches the urethra and the bladder through a conventional duct, formed in the tubular body 4, which however is not illustrated for the sake of simplicity in illustration; the electric power supply is then switched on, activating the ions contained in the drug and thus producing the therapeutic effect in two parts of the body simultaneously.

The drug is introduced in the body by means of the openings 10 formed at the respective terminals 7 and at the ground electrode 8, and the electrical force is transmitted in the same manner.

The invention thus conceived is susceptible to numerous modifications and variations, all of which are within the scope of the inventive concept.

All the details may furthermore be replaced with other technically equivalent elements.

What is claimed is:

1. Device for the combined electropharmacological treatment of the bladder, urethra and prostate comprising a bougie that comprises a flexible tubular body having a distal tip which is provided, at a proximal end, with a connector having at least one inlet, said body having, at a distal end, openings for connection to an outside, an opening in its tip and elastic sealing means for obstructing a prostatic urethra arranged perimetrically around it, said bougie being internally provided with an electrode that comprises at least two independent conductors that slide axially, each conductor having an insulated portion and conducting portions that are mutually spaced.

2. Device according to claim 1, wherein the conducting portion of at least a first one of said conductors is located at the distal end of said bougie and the conducting portion of at least a second one of said conductors is located at a level of the proximal end of the bougie.

3. Device according to claim 2, wherein the conducting portion of said second conductor is spiral-shaped and is coiled around the insulated portion of said first conductor.

4. Device according to claim 2, wherein the conducting portion of said first conductor has, at a distal end, a multidirectional ground electrode that can be extracted through the opening in the tip of the tubular body.

5. Device according to claim 4, wherein said multidirectional ground electrode comprises a spherical center that is rigidly coupled to the end of said first conductor, multiple elastically flexible conducting spokes extending radially from said center.

6. Device according to claim 1, wherein said independent conductors can be powered independently of one another.

7. Device according to claim 1, wherein said independent conductors are two.

8. Device according to claim 7, wherein one of the two conductors is shorter than the other one.

9. Device according to claim 8, wherein the conducting portion of said shorter conductor is spiral-shaped and is coiled around the insulated portion of the second conductor.

10. Device according to claim 8, wherein the longer conductor has, at a distal end, a multidirectional ground electrode that can be extracted through the opening in the tip of the tubular body.

11. Device according to claim 10, wherein said multidirectional ground electrode comprises a spherical center that is rigidly coupled to the end of said longer conductor, multiple elastically flexible conducting spokes extending radially from said center.

12. Device according to claim 1, wherein said elastic sealing means are constituted by a bag that can be dilated during use and that in its active configuration is suitable to obstruct the prostatic urethra upstream of the bladder.

13. Method for the simultaneous electropharmacological treatment of the bladder, urethra and prostate, comprising the steps of:

placing a bougie along a prostatic urethra so that a distal end enters a bladder, inserting an electrode, which is divided into at least two independent conductors of different lengths so as to allow an end of a longer conductor to pass through an opening of a tip of the bougie to allow a multidirectional ground electrode to open out radially inside the bladder and, simultaneously, arranging a second conductor along the prostatic urethra, applying a second external counter-electrode in an external body region at the organs to be treated, electrically connecting said electrode inserted into the bougie to an external circuit that includes an electric current source connected to the external counter-electrode, infusing a solution through an inlet of the connector that comprises at least one drug suitable to treat affections involving the bladder and the prostate and, simultaneously, applying a potential difference between said, electrode and said second external counter-electrode, thereby producing an electric field suitable to cause the migration of said at least one drug into the tissues of the bladder and of the prostate.

14. Treatment method according to claim 13, further comprising the step of supplying a current to said conductors at different potential values to allow differentiated migration of the dissolved ions.

15. Treatment method according to claim 14, further comprising the step of supplying a higher voltage to the electrode located at a more severely affected organ, therefore allowing a larger amount of drug to be administered to tissues that most need to be treated.

16. Treatment method according to claim 13, further comprising the step of supplying a large amount of solution of the drugs in order to dilate the bladder tissue and fill the bladder cavity so that it acts as a solution containment vessel, said solution subsequently flowing out through the prostatic urethra, allowing an additional therapeutic treatment of the urethral tissue.

* * * * *